US00PP19264P3

(12) United States Plant Patent
Pan

(10) Patent No.: US PP19,264 P3
(45) Date of Patent: Sep. 23, 2008

(54) *LANTANA* PLANT NAMED 'BANTE CHERIASUN'

(50) Latin Name: *Lantana camara*
Varietal Denomination: Bante Cheriasun

(75) Inventor: Shifeng Pan, Hollister, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/654,924

(22) Filed: Jan. 17, 2007

(65) Prior Publication Data

US 2008/0184416 P1 Jul. 31, 2008

(51) Int. Cl.
*A01H 5/00* (2006.01)

(52) U.S. Cl. ..... Plt./227

(58) Field of Classification Search ..... Plt./227
See application file for complete search history.

*Primary Examiner*—Anne Marie Grunberg
*Assistant Examiner*—Louanne C Krawczewicz Myers
(74) *Attorney, Agent, or Firm*—Jondle & Associates, P.C.

(57) ABSTRACT

A *Lantana* plant particularly distinguished by deep yellow to rose lavender flowers, a continuous, abundant and mid-season flowering response, medium green foliage with ovate leaves, vigorous, compact growth and good branching ability, is disclosed.

2 Drawing Sheets

Genus and species: *Lantana camara.*
Variety denomination: 'Bante Cheriasun'.

BACKGROUND OF THE NEW PLANT

The present invention comprises a new and distinct cultivar of *Lantana,* botanically known as *Lantana camara* and hereinafter referred to by the cultivar name 'Bante Cheriasun'. The new cultivar originated from a self-pollination made in July 2003 in Gilroy, Calif. of '18-2', a fuchsia (unpatented) proprietary line. A single plant was selected in April 2004 for further propagation.

The new cultivar was created in July of 2003 in Gilroy, Calif. and has been asexually reproduced repeatedly by vegetative cuttings and tissue culture in Gilroy, Calif. and Andijk, The Netherlands over a two and one-half-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for in Germany on Nov. 27, 2006.

SUMMARY OF THE INVENTION

The following are the most outstanding and distinguishing characteristics of the new cultivar when grown under normal horticultural practices in Gilroy, Calif.

1. Deep yellow to rose lavender flowers;
2. A continuous, abundant and mid-season flowering response;
3. Medium green foliage with ovate leaves;
4. Vigorous growth;
5. A compact and mounding plant habit; and
6. Good branching ability.

DESCRIPTION OF THE PHOTOGRAPHS

This new *Lantana* plant is illustrated by the accompanying photographs which show overall plant habit including blooms, buds and foliage of the plant; the colors shown are as true as can be reasonably obtained by conventional photographic procedures. The photos are of 15–16 week-old plants taken in September 2006.

DESCRIPTION OF THE NEW CULTIVAR

Figure 1:
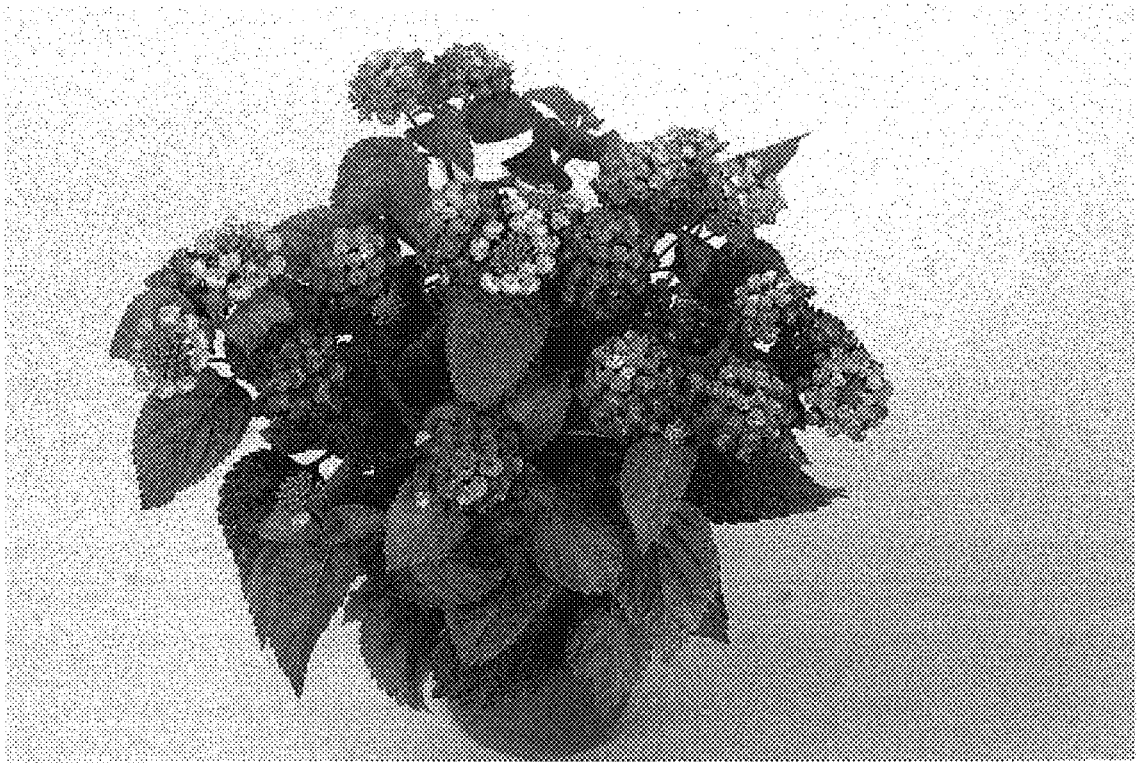
FIG. 1 shows the overall plant habit, including inflorescences, buds and foliage of the whole plant.
Figure 2:
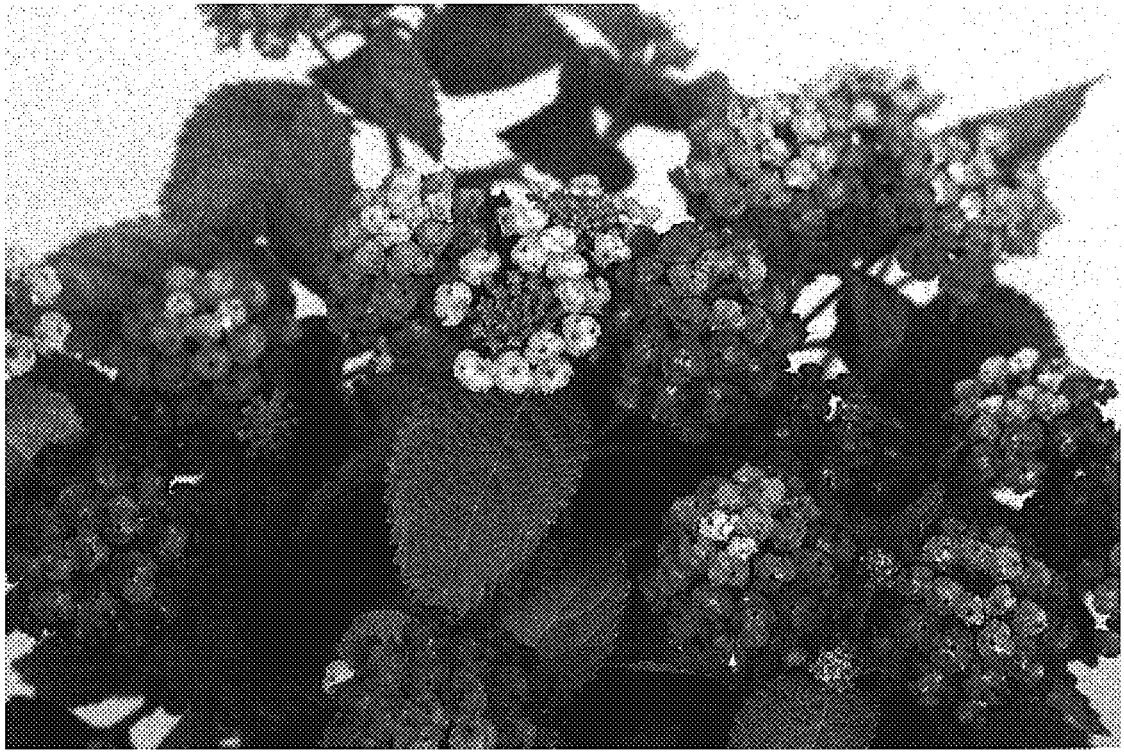
FIG. 2 shows a close-up of several mature inflorescences.

The following detailed descriptions set forth the distinctive characteristics of 'Bante Cheriasun'. The data which define these characteristics were collected from asexual reproductions carried out in Hillscheid, Germany. The plant history was taken on 26-week-old plants, grown in Gilroy, Calif. in 4" pots. Observations were made in summer and early fall. The plants had one plant growth regulator treatment using SUMAGIC at 10 PPM and one terminal pinch after cuttings were transplanted. Color readings were taken under natural light. Color references are primarily to the R.H.S. Colour Chart of The Royal Horticultural Society of London (R.H.S.) (2001 edition).

DETAILED BOTANICAL DESCRIPTION

Classification:
*Family.*—Verbenaceae.
*Botanical.*—*Lantana camara.*
*Denomination.*—'Bante Cheriasun'.
*Common name.*—*Lantana.*

Parentage: Selfing of '18-2', a fuchsia proprietary line (unpatented).

Growth:
*Form.*—Semi-woody, herbaceous; grown as an annual or perennial.
*Growth and branching habit.*—Compact, low mounding, good branching, pinching of the apices enhances the number of branches and results in a tighter plant habit.

*Height* (*measured from the top of the soil*).—23.0 cm to 27.0 cm.

*Width* (*horizontal plant diameter*).—25.0 cm to 30.0 cm.

*Time to produce a finished flowering plant.*—11 to 13 weeks for a 12-cm pot in the Spring.

*Outdoor plant performance.*—Use in containers and hanging baskets.

*Time to initiate and develop roots.*—Approximately 24 days.

*Root description.*—Fibrous, fleshy, white, self-branching.

Stems:

*Number of branches per plant.*—8–10.

*Length.*—10.0 to 15.0 cm.

*Diameter* (*measured from the midpoint*).—0.20 to 0.25 cm.

*Internode length.*—1.5 to 1.9 cm.

*Color.*—Immature (growing) stems: RHS 144A. Mature (woody) stems: Slightly lighter than RHS 163A.

*Anthocyanin.*—Absent.

*Texture.*—Glandular hairs; scabrous.

Leaves:

*Arrangement.*—Opposite.

*Quantity per lateral stem.*—8 to 10.

*Fragrance.*—Slightly spicy.

*Immature leaf.*—Color: Upper surface: Closest to RHS 137A. Lower surface: RHS 137D.

*Mature leaf.*—Color: Upper surface: RHS 147A. Lower surface: RHS 137C. Length: 6.4 cm to 7.2 cm. Width: 4.2 cm to 6.2 cm. Shape: Ovate. Apex: Acute. Base: Attenuate. Margin: Serrate. Texture (both surfaces): Rugose; glandular hairs; scabrous. Venation: Pinnate. Venation color: RHS 137D for the lower surface; the upper surface is indistinct.

*Petioles.*—Length: 1.4 cm. Diameter: 0.2 cm. Color: RHS 137D. Texture: Glandular hairs; scabrous.

Flower buds:

*Shape.*—Tubular.

*Length.*—0.8 cm to 1.0 cm.

*Diameter* (*at the tip*).—0.35 cm.

*Color* (*at tight bud*).—RHS 6B with a touch of RHS 25A at the apex; RHS 31B on the outside of the corolla tube.

Inflorescence:

*Blooming habit.*—Flowers continuously from Spring through Fall; Inflorescences usually appear in pairs from a node with one inflorescence per leaf axil.

*Lastingness of the inflorescence on the plant.*—About one month.

*Fragrance.*—Sweet and slightly spicy.

*Inflorescence type.*—Umbel-like flattened semi-sphere, the florets are sessile on an ovate receptacle.

*Horizontal diameter of inflorescence.*—4.0 cm to 4.5 cm.

*Vertical depth of inflorescence.*—2.0 cm.

*Number of inflorescences per plant.*—20 to 30.

*Number of florets per inflorescence.*—25 to 30.

*Peduncle.*—Length: 1.9 cm to 2.2 cm. Diameter: 0.1 cm to 0.125 cm. Color: RHS 144A. Texture: Glandular hairs, Scabrous and pubescent.

*Pedicels.*—None, flowers are sessile.

Flowers:

*Floret form.*—Salver-shaped to shallow cup-shaped and zygomorphic, with a relatively long tube at the base. Each flower is subtended by a single bract.

*Corolla diameter.*—0.9 cm to 1.0 cm.

*Floret depth.*—1.5 cm.

*General color.*—Mostly yellow-gold in the very opening stages, then turning through varying hues of oranges, with red-purple mature florets. Color intensities can vary with cultural growing conditions. Immature flower (face): Color: Upper surface: A little deeper than RHS 12A, with shades of RHS 29B mostly around the margins. Lower surface: RHS 23D.

*Mature flower* (*face*).—Color: Upper surface: Between RHS 25B and RHS 25C, with a little RHS 12C at the corolla opening; then maturing to RHS 64B; and then fading to between RHS 64C and RHS 63B. Lower surface: RHS 62C. Corolla tube: Length: 1.2 cm to 1.4 cm. Diameter (at opening): 0.2 cm. Color: Outer surface: RHS 62D with some darker shading of RHS 64C in irregular patches. Inner surface: RHS 39D. Texture: Outer surface is densely pubescent and inner surface is pubescent.

*Petals.*—Number and arrangement: Composed of 5 petals fused at the base. Shape: Salver-shaped. Length: 0.6 cm to 0.7 cm. Diameter: 0.6 cm. Apex: Rounded to slightly retuse. Base: Fused. Margin: Entire, slightly ruffled. Degree of separation between the petals: Moderate. Texture (both surfaces): Papillose, with a few hairs showing basally at the corolla opening.

*Bract.*—Color: RHS 144B with RHS 144A at the apex. Length: 0.5 cm to 0.7 cm. Diameter: 0.2 cm. Shape: Short, linear. Apex: Acute. Margin: Entire. Base: Fused. Texture: Glandular hairs, densely pubescent.

*Calyx.*—General: Composed of 5 fused sepals forming a short tube around the base of each floret. Shape: Tube-shaped with two short lobes. Length: 0.15 cm to 0.2 cm. Diameter: 0.2 cm. Color: Upper surface: RHS 144C. Lower surface: Not observed. Apex (of calyx lobe): Obtuse. Base (of sepals): Fused. Margin (of sepals): The tips are shallowly fringed, side margins are fused. Texture: Densely pubescent.

Reproductive organs:

*Stamens.*—Quantity: 4. Filament color: RHS 4C. Filament diameter: 0.6 cm to 0.7 cm. Filament length: 0.05 cm. Anther color: RHS 9A. Anther length: 0.1 cm. Anther shape: 2-lobed, oblong. Pollen amount: Moderate. Pollen color: RHS 4B.

*Pistil.*—Quantity: One. Length: 0.3 cm to 0.4 cm. Stigma color: RHS 145A. Style color: RHS 155C. Style length: 0.25 cm to 0.3 cm.

Fruit/seed set: None observed.

Disease and insect resistance: None observed.

COMPARISON WITH PARENTAL AND COMMERCIAL CULTIVARS

'Bante Cheriasun' differs from the parent '18-2' in that 'Bante Cheriasun' is more vigorous, more compact, is earlier to flower and has more yellow immature flowers than the parent cultivar.

'Bante Cheriasun' differs from the commercial variety 'Bante Rossa' (U.S. Plant Pat. No. 18,148) in that 'Bante Cheriasun' is more compact, has shorter internodes and better branching than 'Banta Rossa'. Additionally, 'Bante Cheriasun' has deeper yellow flowers maturing to deeper rose lavender while 'Bante Rossa' has lighter yellow to rose-pink flowers.

I claim:

1. A new and distinct cultivar of *Lantana* plant as shown and described herein.

* * * * *